(12) United States Patent
Kondo et al.

(10) Patent No.: US 7,596,274 B2
(45) Date of Patent: Sep. 29, 2009

(54) METHOD OF INSPECTING UNEVENNESS OF PARTITION SURFACE OF HONEYCOMB STRUCTURE AND INSPECTING DEVICE

(75) Inventors: Takahiro Kondo, Nagoya (JP); Yoichi Aoki, Nagoya (JP); Akihiro Mizutani, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 608 days.

(21) Appl. No.: 10/577,445

(22) PCT Filed: Oct. 28, 2004

(86) PCT No.: PCT/JP2004/016053

§ 371 (c)(1),
(2), (4) Date: Apr. 27, 2006

(87) PCT Pub. No.: WO2005/040773

PCT Pub. Date: May 6, 2005

(65) Prior Publication Data
US 2007/0091309 A1 Apr. 26, 2007

(30) Foreign Application Priority Data
Oct. 28, 2003 (JP) .............................. 2003-367339

(51) Int. Cl.
*G06K 9/62* (2006.01)
(52) U.S. Cl. .......................... 382/224; 428/116; 55/523; 296/39.1; 382/141; 382/151
(58) Field of Classification Search ................ 428/116, 428/180, 188, 117, 118, 34.4; 52/239, 523, 52/DIG. 30; 502/439, 527.18, 527.19, 527.21; 425/461, 467, 380, 465, 464; 422/174, 180, 422/222, 177, 211; 296/39.1; 356/71; 382/141, 382/224, 145, 151, 149, 304; 55/523
See application file for complete search history.

(56) References Cited

U.S. PATENT DOCUMENTS 4,319,840 A * 3/1982 Kondo et al. ............. 356/241.1

(Continued)

FOREIGN PATENT DOCUMENTS

JP A 54-139784 10/1979

(Continued)

*Primary Examiner*—Sheela C Chawan
(74) *Attorney, Agent, or Firm*—Oliff & Berridge, PLC

(57) ABSTRACT

A method of inspecting unevenness of a partition wall surface of a honeycomb structure includes the steps of: allowing a diffusion light to enter from one end face 8 side by a predetermined lighting means 3 and to exit from the other end face 8 side of the honeycomb structure 2 after passing it through the inside of the cells, allowing the exited diffusion light to pass through a translucent screen 4 disposed on the other end face 9 side of the honeycomb structure 2 to act as a transmitted light, projecting a transmitted image 13 by means of the tone of the transmitted light onto the transmitted light side of the screen 4, picking up the transmitted image 13 projected on the screen 4 by an imaging means 5, and analyzing by an analyzing means 6 the gray level of the obtained image to inspect for each cell the degree of the surface unevenness of the partition walls. This method enables easy inspection on the surface unevenness of the partition walls of the honeycomb structure 2.

20 Claims, 6 Drawing Sheets

U.S. PATENT DOCUMENTS

| | | | |
|---|---|---|---|
| 5,184,190 A * | 2/1993 | Rai et al. | 356/239.1 |
| 5,463,462 A * | 10/1995 | Ohnishi et al. | 356/521 |
| 6,764,743 B2 * | 7/2004 | Kato et al. | 428/118 |

FOREIGN PATENT DOCUMENTS

| | | |
|---|---|---|
| JP | A 5-264459 | 10/1993 |
| JP | A 9-229662 | 9/1997 |
| JP | A 2002-14051 | 1/2002 |
| JP | A 2002-243650 | 8/2002 |
| JP | A 2003-130799 | 5/2003 |
| JP | A 2004-37248 | 2/2004 |

* cited by examiner

METHOD OF INSPECTING UNEVENNESS OF PARTITION SURFACE OF HONEYCOMB STRUCTURE AND INSPECTING DEVICE

TECHNICAL FIELD

The present invention relates to a method of inspecting unevenness of a partition wall surface of a honeycomb structure and an inspecting device. More specifically, the present invention relates to a method of inspecting unevenness of a partition wall surface of a honeycomb structure and an inspecting device capable of simply and nondestructively inspecting unevenness of a partition wall surface of a honeycomb structure, which serves as a yardstick of judging the quality of the honeycomb structure.

BACKGROUND ART

A honeycomb structure is often used as a filter, a catalyst carrier, or the like for, for example, an exhaust gas purification apparatus for a thermal engine such as an internal combustion engine or a combustion device such as a boiler, a reforming device for a liquid fuel or a gaseous fuel, a purification treatment device for service water and sewage, or the like. In particular, a honeycomb structure is suitably used as a diesel particulate filter (DPF) for trapping and removing particulate matter contained in dust-containing fluid such as exhaust gas discharged from a diesel engine or a high-temperature gas dust-trapping apparatus.

A honeycomb structure used for such a purpose traps and removes unnecessary particulate mater when fluid to be treated passes through fine pores in the porous partition walls or brings fluid to be treated into contact with a catalyst loaded on a porous partition wall surface or in the fine pores.

There has conventionally been conducted an inspection of clogging in cells (through-holes) serving as passages of fluid to be treated as one of methods of quality control of a honeycomb structure. A lighting apparatus for this inspection is disclosed (e.g., see Patent Document 1). This lighting apparatus for inspection is provided with a lighting means which has an irradiating angle, the first lens which collects light from the lighting means and converts the light into parallel light, and the second lens which collects the parallel light from the first lens after passing through the object to be inspected so that the light can be taken into an imaging means.

Patent Document 1: JP A 2003-130799.

DISCLOSURE OF THE INVENTION

However, the above lighting apparatus for inspection can inspect only clogging of cells (through-holes), which has been a problem, though it has been desired in recent years to inspect a degree of unevenness of a partition wall surface to load a catalyst uniformly and to realize a low cost and a low pressure loss by reducing the amount of the catalyst to be loaded when a honeycomb structure is used as a filter or a catalyst carrier.

The present invention has been made in view of such circumstances and aims to provide a method of inspecting unevenness of a partition wall surface of a honeycomb structure and an inspecting device capable of simply and nondestructively inspecting unevenness of a partition wall surface of a honeycomb structure, which serves as a yardstick of judging the quality of the honeycomb structure.

To solve the above problems, the present invention provides the following method of inspecting unevenness of a partition wall surface of a honeycomb structure and an inspecting device.

[1] A method of inspecting, for each cell, unevenness of a partition wall surface of a cylindrical honeycomb structure having a plurality of cells functioning as passages for fluid and separated from each other by partition walls,
the method comprising the steps of:
allowing a diffusion light to enter from one end face side of a honeycomb structure by a predetermined lighting means and to exit from the other end face side of the honeycomb structure after passing it through the inside of the cells,
allowing the exited diffusion light to pass through a translucent screen disposed on the other end face side of the honeycomb structure to act as a transmitted light,
projecting a transmitted image by means of the tone of the transmitted light onto the transmitted light side of the screen,
picking up the transmitted image projected on the screen by an imaging means, and
analyzing by an analyzing means the gray level of the obtained image to inspect for each cell the degree of the surface unevenness of the partition walls of the honeycomb structure (hereinbelow sometimes referred to as "first invention").

[2] A method of inspecting unevenness of a partition wall surface of a cylindrical honeycomb structure according to [1], wherein the screen is disposed so as to be in contact with the other end face side of the honeycomb structure.

[3] A method of inspecting, for each cell, unevenness of a partition wall surface of a cylindrical honeycomb structure having a plurality of cells functioning as passages for fluid and separated from each other by partition walls,
the method comprising the steps of:
allowing a diffusion light to enter from one end face side of a honeycomb structure by a predetermined lighting means and to exit from the other end face side of the honeycomb structure after passing it through the inside of the cells,
allowing the exited diffusion light to be picked up by an imaging means for each image from the direction perpendicular to the other end face of the honeycomb structure, and
analyzing by an analyzing means the gray level of the obtained image to inspect for each cell the degree of the surface unevenness of the partition walls of the honeycomb structure (hereinbelow sometimes referred to as "second invention").

[4] A method of inspecting unevenness of a partition wall surface of a cylindrical honeycomb structure according to any one of [1] to [3], wherein the gray level of the image is analyzed by being subjected to a binary treatment with the analyzing means.

[5] A method of inspecting unevenness of a partition wall surface of a cylindrical honeycomb structure according to any one of [1] to [4], wherein a shadow generated by the partition walls in the image is removed before the gray level of the image is analyzed by the analyzing means.

[6] A method of inspecting unevenness of a partition wall surface of a cylindrical honeycomb structure according to any one of [1] to [5], wherein the diffusion light from the lighting means has an illuminance of 3000 Lux or more.

[7] A method of inspecting unevenness of a partition wall surface of a cylindrical honeycomb structure according to any one of [1] to [6], wherein the screen has a light transmittance of 35 to 90%.

[8] An inspecting device for inspecting, for each cell, unevenness of a partition wall surface of a cylindrical honeycomb structure having a plurality of cells functioning as passages for fluid and separated from each other by partition walls, the inspecting device comprising:
  a lighting means disposed on one end face side of the honeycomb structure and allowing a diffusion light to enter from one end face side of a honeycomb structure and to exit from the other end face side of the honeycomb structure after passing it through the inside of the cells,
  a translucent screen disposed on the other end face side of the honeycomb structure, allowing the exited diffusion light to pass therethrough to obtain a transmitted light, and capable of projecting a transmitted image by means of the tone of the transmitted light onto the transmitted light side of the screen,
  an imaging means for picking up the transmitted image projected on the screen, and
  an analyzing means for analyzing the gray level of the image picked up by the imaging means to inspect for each cell the level of the surface unevenness of the partition walls of the honeycomb structure(hereinbelow sometimes referred to as "third invention").

[9] An inspecting device for inspecting unevenness of a partition wall surface of a cylindrical honeycomb structure according to [8], wherein the screen is disposed so as to be in contact with the other end face side of the honeycomb structure.

[10] An inspecting device for inspecting, for each cell, unevenness of a partition wall surface of a cylindrical honeycomb structure having a plurality of cells functioning as passages for fluid and separated from each other by partition walls, the inspecting device comprising:
  a lighting means disposed on one end face side of the honeycomb structure and allowing a diffusion light to enter from one end face side of a honeycomb structure and to exit from the other end face side of the honeycomb structure after passing it through the inside of the cells,
  an imaging means disposed on the other end face side of the honeycomb structure and allowing the exited diffusion light to be picked up for each cell from the direction perpendicular to the other end face of the honeycomb structure, and an analyzing means for analyzing the gray level of the image picked up by the imaging means to inspect for each cell the level of the surface unevenness of the partition walls of the honeycomb structure from a result of analysis by the analyzing means (hereinbelow sometimes referred to as "fourth invention").

[11] An inspecting device for inspecting unevenness of a partition wall surface of a cylindrical honeycomb structure according to any one of [8] to [10], wherein the gray level of the image is analyzed by being subjected to a binary treatment with the analyzing means.

[12] An inspecting device for inspecting unevenness of a partition wall surface of a cylindrical honeycomb structure according to any one of [8] to [11], wherein a shadow generated by the partition walls in the image is removed before the gray level of the image is analyzed by the analyzing means.

[13] An inspecting device for inspecting unevenness of a partition wall surface of a cylindrical honeycomb structure according to any one of [8] to [12], wherein the diffusion light from the lighting means has an illuminance of 3000 Lux or more.

[14] An inspecting device for inspecting unevenness of a partition wall surface of a cylindrical honeycomb structure according to any one of [8] to [13], wherein the screen has a light transmittance of 35 to 90%.

According to the present invention, there can be provided a method of inspecting unevenness of a partition wall surface of a honeycomb structure and an inspecting device capable of simply inspecting unevenness of a partition wall surface of a honeycomb structure, which serves as a yardstick of judging the quality of the honeycomb structure.

BRIEF DESCRIPTION OF THE DRAWINGS

FIG. 7($b$) is an explanatory view showing an image obtained by an imaging means when a honeycomb structure was inspected by using a device for inspecting unevenness of a partition wall surface of a honeycomb structure in an Example of the present invention.

FIG. 7($c$) is an explanatory view showing an image obtained by an imaging means when a honeycomb structure was inspected by using a device for inspecting unevenness of a partition wall surface of a honeycomb structure in an Example of the present invention.

FIG. 8($b$) is an explanatory view showing the results of a binary treatment of an image shown in FIG. 7($a$).

FIG. 8($c$) is an explanatory view showing the results of a binary treatment of an image shown in FIG. 7($a$).

Figure 1:
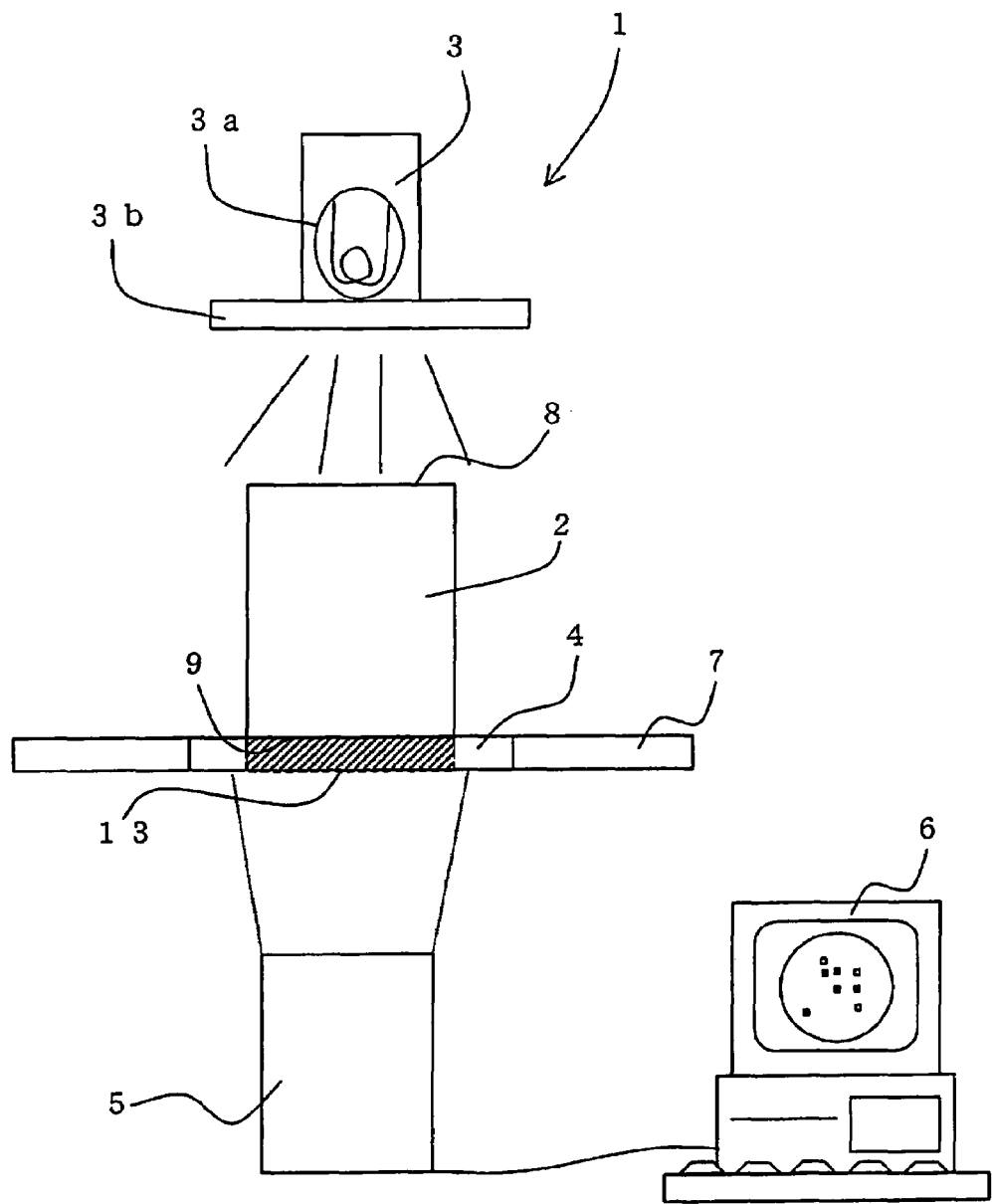
FIG. 1 is a plan View schematically showing an embodiment of an inspecting device for inspecting unevenness of a partition wall surface of a honeycomb structure of the present invention (third invention).

REFERENCE NUMERALS 1. device for inspecting unevenness of a partition wall surface of a honeycomb structure (unevenness inspection method), 2. honeycomb structure, 3. lighting means, 3$a$. frosted glass, 4. screen, 5. imaging means, 6. analyzing means, 7. base, 8. one end face, 9. the other end face, 11. partition wall, 12. cell, 13. transmitted image, 14. image, 15. shadow, 21. device for inspecting unevenness of a partition wall surface of a honeycomb structure, 23. lighting means, 23$b$. frosted glass, 25. imaging means, 26. analyzing means

BEST MODE FOR CARRYING OUT THE INVENTION

A mode for carrying out a method of inspecting unevenness of a partition wall surface of a honeycomb structure and an inspecting device of the present invention (first to fourth inventions) will hereinbelow be described with referring to drawings.

Figure 2:
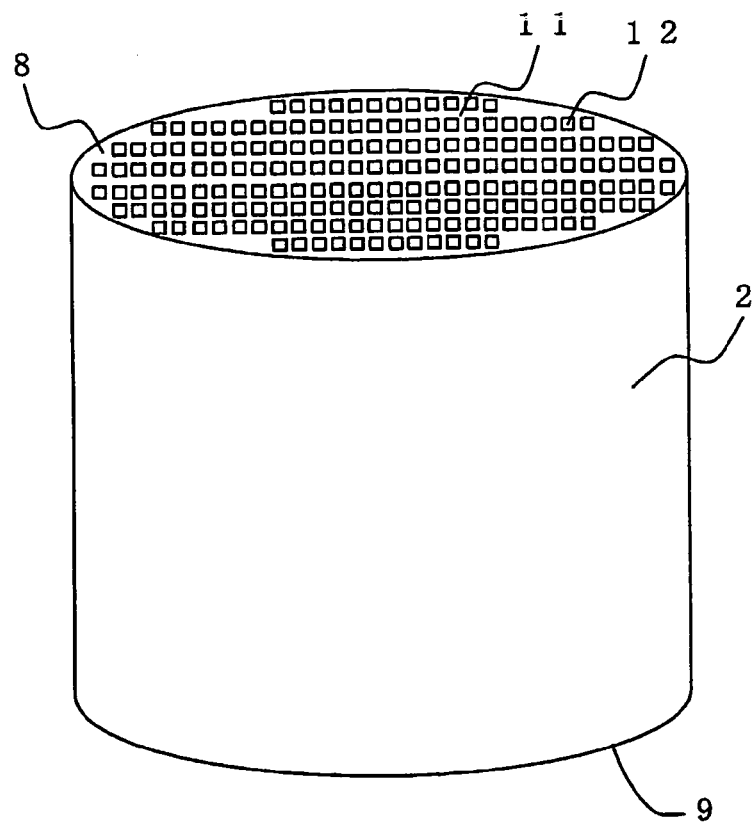
FIG. 2 is a perspective view showing a honeycomb structure to be inspected of an embodiment of a method for inspecting unevenness of a partition wall surface of a honeycomb structure of the present invention (first invention).

First, an embodiment of a method of inspecting unevenness of a partition wall surface of a honeycomb structure of the first invention will concretely be described with referring to drawings, and in the description, an embodiment of a device for inspecting unevenness of a partition wall surface of a honeycomb structure of the third invention will be described at the same time. FIG. 1 is a plan view schematically showing an embodiment of a device for inspecting unevenness of a partition wall surface of a honeycomb structure of the third invention. FIG. 2 is a perspective view showing a honeycomb structure to be inspected by a method of inspecting unevenness of a partition wall surface of a honeycomb structure of the present embodiment.

A method of inspecting unevenness of a partition wall surface of a honeycomb structure of the present embodiment can be realized by using, for example, the device for inspecting unevenness of a partition wall surface of a honeycomb structure shown in FIG. 1. Specifically, a method of inspecting unevenness of a partition wall surface of a honeycomb structure of the present embodiment is a method of inspecting, for each cell 12, unevenness of a surface of the partition walls 11 of a honeycomb structure in which unevenness of a surface of partition walls 11 of a cylindrical honeycomb structure 2 having a plurality of cells 12 functioning as passages for fluid by the partition walls 11 and separated from each other by partition walls 11. As shown in FIGS. 1 and 2, a method of inspecting unevenness of a partition wall surface of a honeycomb structure includes the steps of: allowing a diffusion light to enter from one end face 8 side by a predetermined lighting means 3 and to exit from the other end face 8 side of the honeycomb structure 2 after passing it through the inside of the cells 12, allowing the exited diffusion light to pass through a translucent screen 4 disposed on the other end face 9 side of the honeycomb structure 2 to act as a transmitted light, projecting a transmitted image 13 by means of the tone of the transmitted light onto the transmitted light side of the screen 4, picking up the transmitted image 13 projected on the screen 4 by an imaging means 5, and analyzing by an analyzing means 6 the gray level of the obtained image to inspect for each cell the level of the surface unevenness of the partition walls 11.

In addition a device 1 for inspecting unevenness of a partition wall surface of a honeycomb structure of the present embodiment is a device 1 for inspecting unevenness of a partition wall surface of a honeycomb structure inspecting, for each cell, a level of a partition wall surface of a cylindrical honeycomb structure 2 having a plurality of cells 12 functioning as passages for fluid and separated from each other by partition walls 11, the inspecting device having:

a lighting means 3 allowing a diffusion light to enter from one end face 8 side of a honeycomb structure and to exit from the other end face 9 side of the honeycomb structure 2 after passing it through the inside of the cells 12, a translucent screen 4 allowing the diffusion light exited from the other end 9 face to pass therethrough to obtain a transmitted light, and capable of projecting a transmitted image 13 by means of the tone of the transmitted light onto the transmitted light side of the screen 4, an imaging means 5 for picking up the transmitted image 13 projected on the screen 4, and an analyzing means 6 for analyzing the gray level of the image picked up by the imaging means 5 to inspect for each cell 12 the level of the surface unevenness of the partition walls 11 of the honeycomb structure. According to a thus constituted device for inspecting unevenness of a partition wall surface of a honeycomb structure, inspection of unevenness of a partition wall surface of a honeycomb structure 2, which serves as a yardstick of judging the quality of the honeycomb structure 2 can be conducted simply and nondestructively.

A method of inspecting unevenness of a partition wall surface of a honeycomb structure of the present embodiment (hereinbeiow sometimes referred to simply as "unevenness inspection method") will hereinbelow be described more specifically.

First, in an unevenness inspection method of the present embodiment, a honeycomb structure 2 to be inspected is disposed on a device 1 for inspecting unevenness of a partition wall surface of a honeycomb structure (hereinbelow sometimes referred to simply as "unevenness inspection device 1"). The unevenness inspection device 1 shown in FIG. 1 has seven bases 7 to which a honeycomb structure 2 is attached. Each of the bases 7 has a screen 4 on which transmitted light is projected. In the unevenness inspection device 1, a lighting means 3 is disposed over the bases 7, and an imaging means 5 is disposed under the screen 4 of the base 7. Therefore, a honeycomb structure 2 to be inspected is disposed on the screen 4 of the base 7 in a state that the other end face 9 side faces downward (is brought into contact with the screen 4). Incidentally, in the case that the positional relation of the lighting means 3 and the imaging means 5 is different from that of FIG. 1, the honeycomb structure 2 may be arranged in such a manner that a diffusion light from a lighting means 3 is allowed to enter from one end face 8 side of a honeycomb structure by a predetermined lighting means and to exit from the other end 9 face side.

The lighting means 3 used in an unevenness inspection device 1 of the present invention is not particularly limited as long as it can suitably irradiate a diffusion light, and there may suitably used a lighting means 3 constituted by, for example, a conventionally known illuminator 3a such as an incandescent electric lamp, a halogen lamp, a fluorescent lamp, a LED, a metal halide lamp, and a xenon lamp and a frosted glass 3b which allows a light from the illuminator to pass therethrough to give a diffusion light. Specifically, a plane illuminator having a plurality of fluorescent lamps or LEDs arranged on the surface thereof or a plane illuminator in which a light irradiated from a predetermined light source is introduced inside an optical fiber to make the light diffused at the tip thereof can be employed as a suitable example.

Though, in an unevenness inspection device 1 of the present invention, illuminance of the diffusion light from the lighting means 3 is not particularly limited, it is preferably 3000 Lux or more, more preferably 20000 to 30000 Lux, and particularly preferably 26000 to 28000 Lux so that tone difference of the diffusion light passed through the cells is clearly recognized.

In addition, less nonuniformity of brightness of a plane illuminator of a lighting means 3 is better. However, in the present embodiment, the ratio of the minimum luminosity to the maximum luminosity in an emission plane of the lighting means 3 is preferably 60% or more, and more preferably 80% or more. This constitution makes correction of an image unnecessary or easy even if correction is performed.

In addition, an unevenness inspection method of the present embodiment is preferably constituted in such a manner that a diffusion light irradiated from the lighting means 3 uniformly enters to the whole surface of one end face 8 of the honeycomb structure 2 to be inspected.

The diffusion light irradiated from the lighting means 3 enters from one end face 8 side of a honeycomb structure 2 and to exit from the other end face 9 side of the honeycomb structure 2 after passing it through the inside of the cells 12. At this time, in the case that a surface of partition walls 11 separating and forming the cells 12 is relatively flat, the diffusion light which entered from one end face 8 side proceeds towards the other end face 9 side with being reflected by the partition walls 11 inside the cells 12. Therefore, most of the diffusion light which enters from one end face 8 side of a honeycomb structure 2 exits from the other end face 9 side.

On the other hand, in the case that unevenness is present on a surface of the partition walls 11, for example, a diffusion light which enters from one end face 8 side of a honeycomb structure 2 has an increased number of reflections due to the unevenness on a surface of the partition walls 11 and lose energy for every time of reflection, thereby lowering the brightness of the diffusion light which exits from the other end face 9 side. There is a constitution that a surface of the partition walls 11 separating and forming cells 12 is perpendicular to the traveling direction of the diffusion light. In such a case, the diffusion light which enters from one end face 8 side may be reflected to the opposite side of the traveling direction upon reflection by the partition walls 11 to lower the brightness of the diffusion light which exits from the other end face 9 side of the honeycomb structure. By the above reason, the brightness of the diffusion light which exits from the other end face 9 side differs between the case of a uneven surface on the partition walls 11 and the case of a even surface on the partition walls 11, that is, the case of a relatively flat surface on the partition walls 11.

Incidentally, in the unevenness inspection device 1 shown in FIG. 1, a diffusion light is used as a light irradiated from the lighting means 3. For example, in the case that not a diffusion light but a parallel light is used as a light irradiated from the lighting means 3, most of the light which enters from one end face 8 side of the honeycomb structure 2 straightly exits from the other end face 9 side without being reflected by the unevenness of a surface of the partition walls 11 (see FIG. 2) and therefore difference in brightness to be generated due to reflection by the unevenness of the surface of the partition walls 11 (see FIG. 2) cannot be recognized. In addition, since a diffusion light is thus used, even in the case that a honeycomb structure 2 to be inspected is set up with a little leaning with respect to a direction of the light irradiated from the lighting means 3, the diffusion light can be passed inside the cells 12 (see FIG. 2), and the diffusion light having a sufficient brightness for inspection can exit from the other end 9 face. For example, when a parallel light is used in case that a honeycomb structure is set up on a base 7 in the state that it is slightly leaning, the amount of light which exits from the other end face 9 side of the honeycomb structure 2 abruptly reduces since the direction of traveling direction of the light irradiated from the lighting means 3 is not parallel to the direction of the central axis of the cells 12 (see FIG. 2), and thereby precise inspection cannot be conducted.

Next, the diffusion light allowed to exit from the other end face 9 side of the honeycomb structure 2 is allowed to pass through a translucent screen 4 to act as a transmitted light, and a transmitted image is projected by means of the tone of the transmitted light on a surface on the transmitted light side of the screen 4. If an imaging means 5 is disposed in a state that a central portion on the other end face 9 side of the honeycomb structure 2 can perpendicularly be picked up and the image on the other end face 9 side of the honeycomb structure 2 is directly picked up without using the screen 4, the whole amount of the light allowed to exit from a peripheral portion of the other end face 9 of the honeycomb structure 2 cannot be picked up due to the angle of view of the imaging means 5, and thereby the problem arises that the light allowed to exit from the peripheral portion of the other end face 9 is picked up darkly. In the unevenness inspection device 1 shown in FIG. 1, the above problem arising due to the angle of view is solved by two-dimensionally indicating the other end face 9 side of the honeycomb structure 2 by using the screen 4. In addition, difference in tone of the diffusion light passed through each of the cells 12 can be indicated as the gray level of the transmitted image, which makes visual recognition easy.

Incidentally, in an unevenness inspecting method of the present invention, the screen 4 is preferably disposed in a state that it is in contact with the other end face 9 side of the honeycomb structure 2 as shown in FIG. 1. This constitution can project the transmitted image 13 more clearly and improve resolution.

The screen 4 used in an unevenness inspection method of the present embodiment has a light transmittance of preferably 35 to 90%, and more preferably 40 to 80%. For such a screen 4, for example, translucent frosted glass, or tracing paper may suitably be used.

Figure 3:
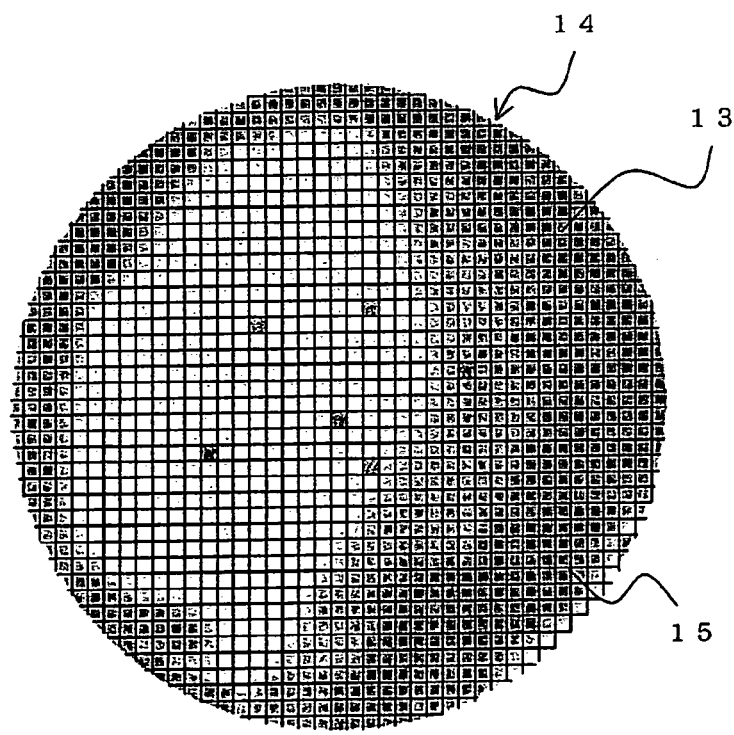
FIG. 3 is an explanatory view showing an image picked up by an imaging means in an embodiment of a method for inspecting unevenness of a partition wall surface of a honeycomb structure of the present invention (first invention).

Next, the transmitted image 13 projected on the screen 4 is picked up by an imaging means 5. As the imaging means 5, a camera, a video camera, a CCD camera, or a CMOS camera can suitably be used. As shown in FIG. 3, in the image 14 obtained by the imaging means 3 (see FIG. 1), the gray level of the transmitted image 13 projected on a screen 4 (see FIG. 1) is picked up. Here, FIG. 3 is an explanatory view showing an image taken by the imaging means in a method of inspecting unevenness of a partition wall surface of a honeycomb structure of the present embodiment. When a surface of the partition walls 11 is relatively flat in a honeycomb structure 2 shown as in FIG. 2, a diffusion light after passing the cells 12 does not lose brightness relatively in an image 14 shown in FIG. 3, and the transmitted image 13 passed through the screen 4 (see FIG. 1) is projected lightly (brightly). When there is much unevenness on a surface of the partition walls 11 of the honeycomb structure 2, the diffusion light allowed to exit from the other end face 9 side becomes darker when it is reflected by the partition walls 11, and the transmitted image 13 (see FIG. 3) passed through the screen 4 (see FIG. 1) is projected deeply (darkly) by the shadow.

From the above, a level of a surface of the partition walls though which the diffusion light passed can be known by analyzing the gray level of the transmitted image 13 of the image 14 as shown in FIG. 3 conversely. To be more concrete, a portion where the transmitted image 13 is projected faintly in the image 14 obtained means that a surface of the partition walls 11 (see FIG. 2) corresponding to the portion is relatively flat. A portion where the transmitted image 13 is projected deeply means that a surface of the partition walls 11 (see FIG. 2) corresponding to the portion is relatively uneven. When a specific standard for judgment is set, a surface of the partition walls 11 (see FIG. 2) is judged to have unevenness in the case that the brightness is lower than a predetermined value in the portion where the transmitted image 13 is projected, and it is preferable to calculate a ratio of the area of the portion where the transmitted image 13 was projected deeply (a portion judged to have unevenness) with respect to the whole area of the transmitted image 13 in the image 14 which was picked up. This constitution enables quality of the targeted honeycomb structure to be inspected easily.

As a more specific method of analysis, there is a suitable method of analysis by subjecting the gray level of the image 14 to a binary treatment. By subjecting the gray level of the image 14 to a binary treatment, inspection having high accuracy and secure reproducibility can be conducted.

In the image 14 obtained by the imaging means 5 (see FIG. 5), a shadow 15 generated by the partition walls 11 (see FIG. 2) is projected in a lattice pattern. The shadow 15 sometimes affects the results of the analysis, and sometimes, accurate inspection results cannot be obtained. Therefore, in the analysis of unevenness of the present embodiment, it is preferable to remove the shadow 15 generated by the partition walls 11 (see FIG. 2) in the image 14 before the gray level of the image 14 is analyzed. Specifically, there is a method in which the obtained image 14 is measured for brightness for each portion corresponding to each cell 12 (see FIG. 2), the shadow 15 due to the partition walls 11 (see FIG. 2) projected in a lattice pattern is regarded as a high frequency component, which is removed with a low path filter. By this operation, the unnecessary shadow 15 (see FIG. 3) is removed as shown in FIG. 4, the image 14 where only the necessary transmitted image 13 is projected can be obtained, and precision of the analysis can further be improved.

Figure 4:
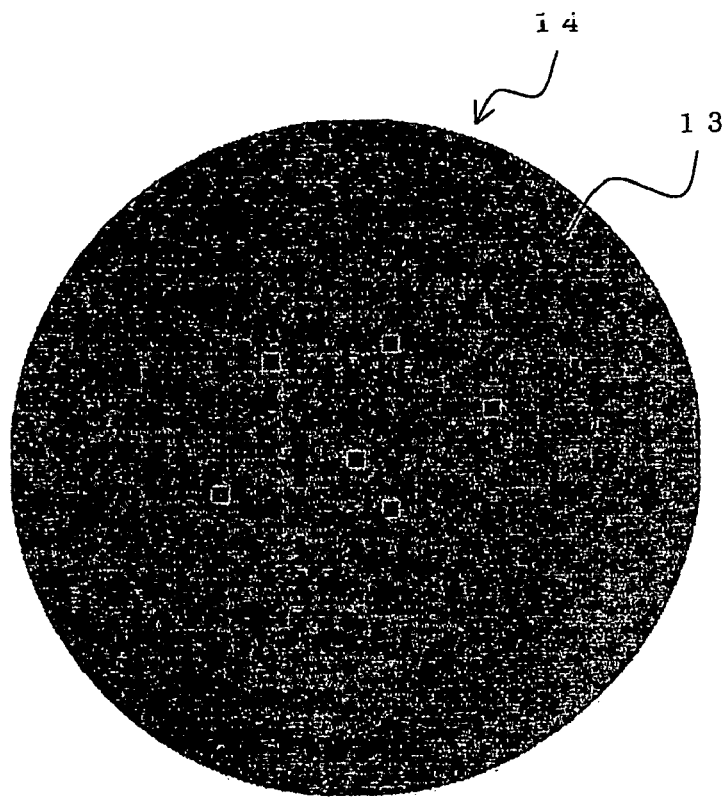
FIG. 4 is an explanatory view showing an image from which a shadow generated by the partition walls is removed in an embodiment of a method for inspecting unevenness of a partition wall surface of a honeycomb structure of the present invention (first invention).

In the case that the transmitted image 13 has uneven brightness in the obtained image 14 as shown in FIG. 4, the obtained image 14 is preferably corrected to obtained the image 14 constituted by the gray level of the transmitted image 13 corresponding to each cell 12 (see FIG. 2). As a specific method, there is a suitable method in which, in the first place, light irradiated from the lighting means 3 is projected on the screen 4 in the state that the honeycomb structure 2 is not set up to pick up an image (not shown) which serves as a background of the light irradiated from the lighting means 3 in the unevenness inspection device 1 shown in FIG. 1, the aforementioned measurement is then conducted with the honeycomb structure 2 being set up on the unevenness inspection device 2 to obtain the image 14 as shown in FIG. 4, and brightness of the obtained image 14 is measured by each portion, the brightness of the previously obtained image (not shown) serving as a background is divided into each of the portions with respect to the obtained image 14 to correct brightness of the whole image 14.

Figure 5:
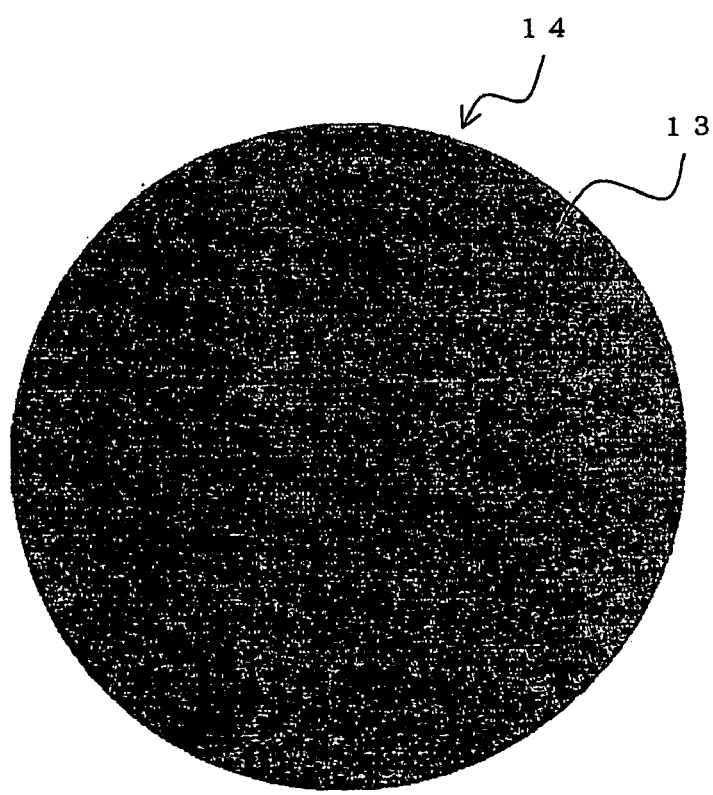
FIG. 5 is an explanatory view showing an image subjected to compensation of brightness in an embodiment of a method for inspecting unevenness of a partition wall surface of a honeycomb structure of the present invention (first invention).

Incidentally, regarding the judgment of the quality of the targeted honeycomb structure 2 (see FIG. 1), it is preferable that the gray level of the image 14 as shown in any of FIGS. 3 to 5 is analyzed by a binary treatment to judge by the ratio of the area of the portion where the transmitted image 13 is projected deeply to the whole area of the transmitted image 13 in the image 14. When the ratio is low, the ratio of flatness on the surface of the partition walls 11 shown in FIG. 2 is high, which means that the honeycomb structure 2 has high quality. When the ratio is high, the ratio of unevenness on the surface of the partition walls 11 is high, which means that the honeycomb structure 2 has low quality. As another method of judging the quality, there is a judgment method in which a distribution is checked, or the like. There are, for example, a method of judging quality of a honeycomb structure in which the predetermined number or more of cells assemble as inferior quality, a method of judging quality of a honeycomb structure in which a portion of a deep shadow is present in a portion of a several mm from the outermost periphery as an inferior quality, and a method of judging quality of a honeycomb structure assembling in the central portion as inferior quality.

As the analyzing means 6 (see FIG. 1) used for an unevenness inspection method of the present embodiment, there can suitably be used a computer which executes a program necessary for a predetermined analysis and can analyze the image picked up by the imaging means 5 by conducting, for example, a binary treatment.

As a standard for the inspection of the honeycomb structure in an unevenness inspection method of the present embodiment, the lower the ratio of the area of a darkly projected portion of the transmitted image 13 is, the less the unevenness of a surface of the partition walls is, and the higher the quality is. Incidentally, it is preferable that a specific value of the above ratio is suitably selected depending on a use or the like of a targeted honeycomb structure. By such a constitution, unevenness of a partition wall surface of a cylindrical honeycomb structure in which a plurality of cells serving as passages for fluid are separated from each other and formed can be inspected simply and nondestructively for each cell.

In an unevenness inspecting method of the present embodiment, the inspection can be conducted even in the case that a catalyst is loaded on the surface and the inside of the partition walls of a targeted honeycomb structure though it is not illustrated. In the case that a catalyst is thus loaded on the surface and the inside of the partition walls, the condition of unevenness of the partition wall surface changes depending of the condition of the catalyst loaded on the partition walls. Therefore, when a honeycomb structure having a catalyst loaded thereon is inspected, it is not just the investigation of unevenness of the partition wall surface, but the investigation of unevenness of the catalyst loaded on the partition wall surface. By using this method, loading conditions of a catalyst, that is, if the catalyst is uniformly loaded can be inspected, for example, when the honeycomb structure is used for a catalyst carrier.

Figure 6:
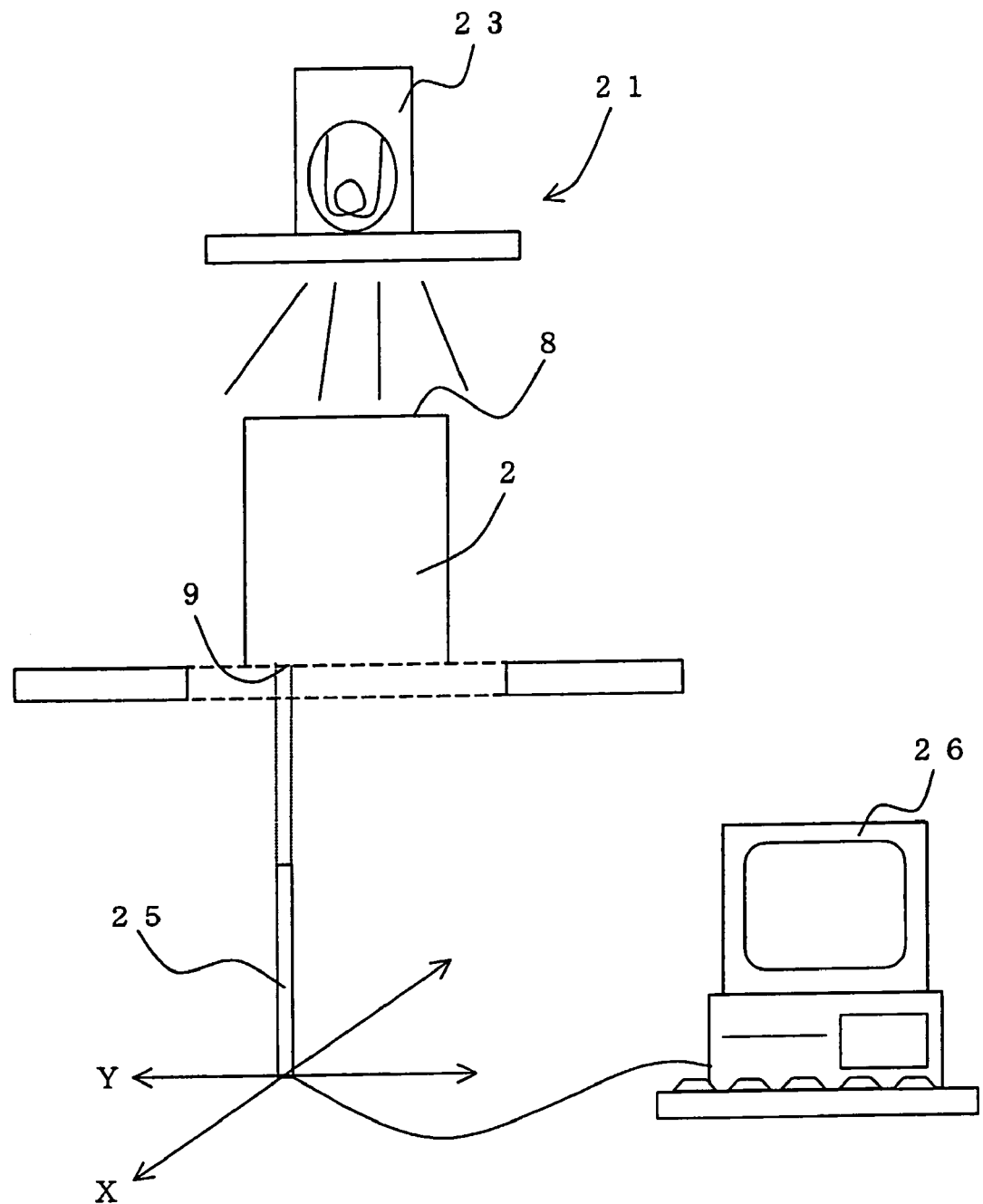
FIG. 6 is a plan view schematically showing an embodiment of a method for inspecting unevenness of a partition wall surface of a honeycomb structure of the present invention (fourth invention).

Next, an embodiment of a method of inspecting unevenness of a partition wall surface of a honeycomb structure of the second invention will specifically be described with referring to FIG. 6, and during the description, an embodiment of a device for inspecting unevenness of a partition wall surface of a honeycomb structure of the fourth invention will be described together. FIG. 6 is a plan view schematically showing an embodiment of a device for inspecting unevenness of a partition wall surface of a honeycomb structure of the fourth invention.

A method for inspecting unevenness of a partition wall surface of a honeycomb structure of the present invention can be realized by using a device 21 for inspecting unevenness of a partition wall surface of a honeycomb structure shown in FIG. 6. Specifically, it is a method for inspecting unevenness of a partition wall surface of a honeycomb structure, in which a level of a surface of the partition walls 11 of a cylindrical honeycomb structure 2 in which a plurality of cells 12 serving as passages of fluid is separated from each other and formed as shown in FIG. 2 is inspected for each cell 12. As shown in FIGS. 2 and 6, diffusion light is allowed to enter from one end face side 8 of a honeycomb structure 2 by a predetermined lighting means 23 and to exit from the other end face 9 side of the honeycomb structure 2 after passing it through the inside of the cells 12, the exited diffusion light is allowed to be picked up by an imaging means 25 for each cell 12 from the direction perpendicular to the other end face 9 of the honeycomb structure 2, and the gray level of the obtained image is analyzed by an analyzing means 26 to inspect for each cell 12 the level of the surface unevenness of the partition walls of the honeycomb structure.

In addition, as shown in FIGS. 2 to 6, a device 21 for inspecting unevenness of a partition wall surface of a honeycomb structure of the present embodiment is provided with a lighting means 23 disposed on one end face 8 side of the honeycomb structure 2 and allowing a diffusion light to enter from one end face 8 side of a honeycomb structure 2 and to exit from the other end face 9 side of the honeycomb structure 2 after passing it through the inside of the cells 12, an imaging means 25 disposed on the other end face 9 side of the honeycomb structure 2 and allowing the exited diffusion light to be picked up for each cell 12 from the direction perpendicular to the other end face 9 of the honeycomb structure 2, and an analyzing means 26 for analyzing the gray level of the image picked up by the imaging means 25 to inspect for each cell 12 the level of the surface unevenness of the partition walls 11 of the honeycomb structure from a result of analysis by the analyzing means 26. According to a device 21 having such constitution for inspecting unevenness of a partition wall surface of a honeycomb structure, unevenness of a partition wall surface of a honeycomb structure, which serves as a yardstick of judging the quality of the honeycomb structure, can be inspected simply and nondestructively.

A method for inspecting unevenness of a partition wall surface of a honeycomb structure of the present embodiment (hereinbelow sometimes referred to as simply "unevenness inspection method") is constituted in the same manner as one embodiment of the first invention except that a diffusion light allowed to exit from the other end face 9 side of the honeycomb structure 2 is picked up by the imaging means 25 for each cell from a direction perpendicular to the other end face 9 of the honeycomb structure 2 in addition to a series of processes of allowing the diffusion light exited from the other end face 9 (see FIG. 1) side of the honeycomb structure 2 (see FIG. 1) to pass through a translucent screen 4 (see FIG. 1) disposed on the other end face 9 (see FIG. 1) side of the honeycomb structure 2 (see FIG. 1) to act as a transmitted light, projecting a transmitted image 13 (see FIG. 1) by means of the tone of the transmitted light onto the transmitted light side surface of the screen 4 (see FIG. 1), and picking up the transmitted image 13 (see FIG. 1) projected on the screen 4 (see FIG. 1) by an imaging means 5 (see FIG. 1) in one embodiment (a method of inspecting unevenness of a partition wall surface of a honeycomb structure) of the first invention.

Similarly, a device 21 for inspecting unevenness of a partition wall surface of a honeycomb structure of the present embodiment is constituted in the same manner as the unevenness inspecting device 1 shown in FIG. 1 except that the device 21 is provided with the imaging means 25 which picks up the diffusion light allowed to exit from the other end face 9 side for each cell 12 from a direction perpendicular to the other end face 9 of the honeycomb structure 2 instead of screen 4 and the imaging means 5 in the unevenness inspection device 1 shown in FIG. 1.

As the imaging means 25 used in the unevenness inspection method of the present embodiment, there may suitably be used, for example, an audio-visual system using telecentric lens or a contact type sensor. Even in the image-picking up system where the angle of view is generated, it can suitably be used by selectively using a portion having less influence of the angle of view in the image picked up. By using such a contact type sensor, a diffusion light allowed to exit from the other end face 9 side of the honeycomb structure 2 is picked up in order for each cell 12 from the direction perpendicular to the other end face 9 of the honeycomb structure 2 to obtain partial images, which are then combined to obtain the whole one image. By using the imaging means 25, influence of the angle of view of the imaging means 5 is eliminated even without using the screen 4 (see FIG. 1), and thereby inspection of unevenness of a partition wall surface of a honeycomb structure can be conducted more effectively. Incidentally, in the unevenness inspection device 21 shown in FIG. 6, the imaging means 25 is constituted so that it is movable in XY direction. However, the device may have a constitution in which the imaging means 25 is fixed and the honeycomb structure is movable.

The image obtained in such a manner is analyzed by the analyzing means 26. It is preferable that the analysis is conducted in the same manner as in an embodiment of the first invention. As the lighting means 23 and the analyzing means 26 constituting the unevenness inspection device 21 shown in FIG. 6, there may suitably be used the ones constituted in the same manner as the lighting means 3 and the analyzing means 6 shown in FIG. 1.

EXAMPLE

Figure 7A:
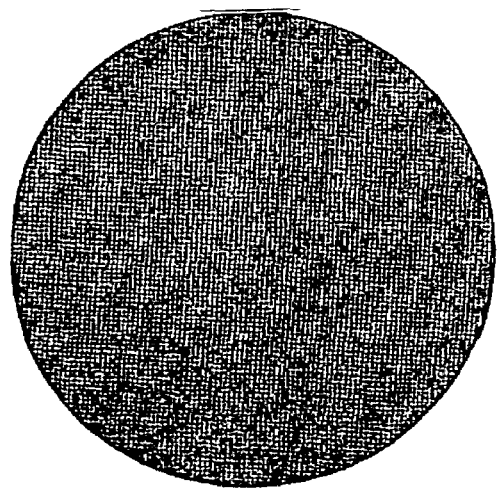
FIG. 7($a$) is an explanatory view showing an image obtained by an imaging means when a honeycomb structure was inspected by using a device for inspecting unevenness of a partition wall surface of a honeycomb structure in an Example of the present invention.
Figure 7B:
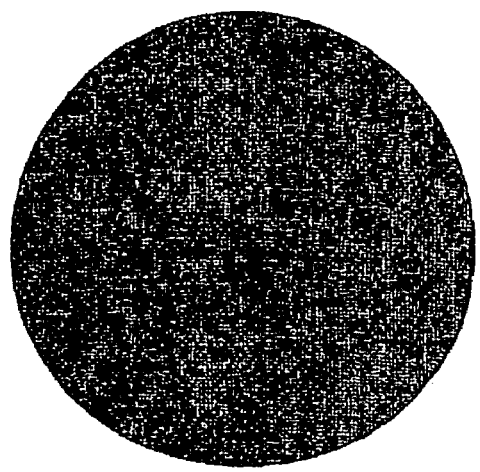
Figure 7C:
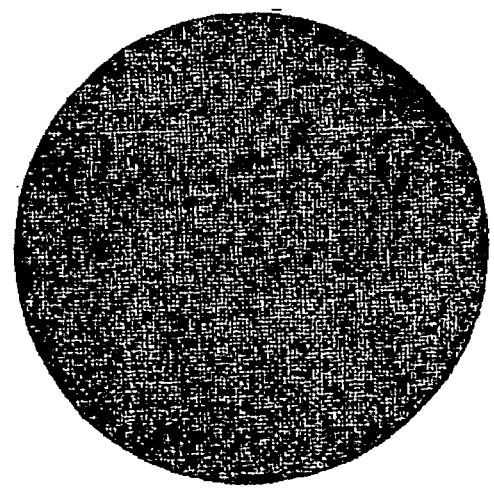
Figure 8A:
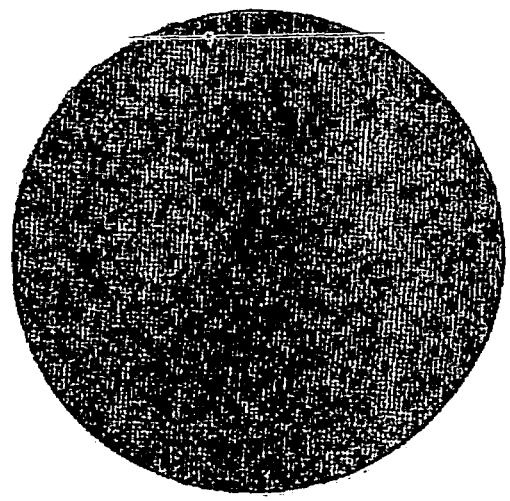
FIG. 8($a$) is an explanatory view showing the results of a binary treatment of an image shown in FIG. 7($a$).
Figure 8B:
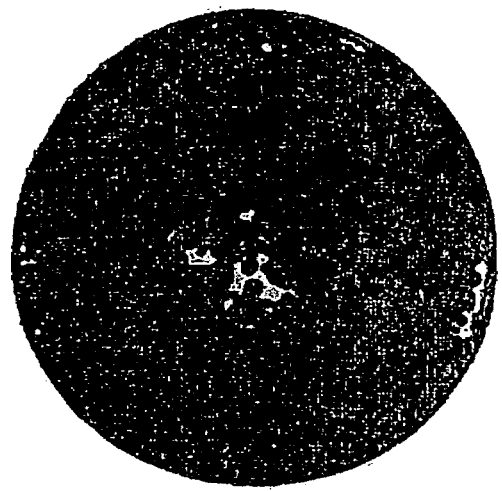
Figure 8C:
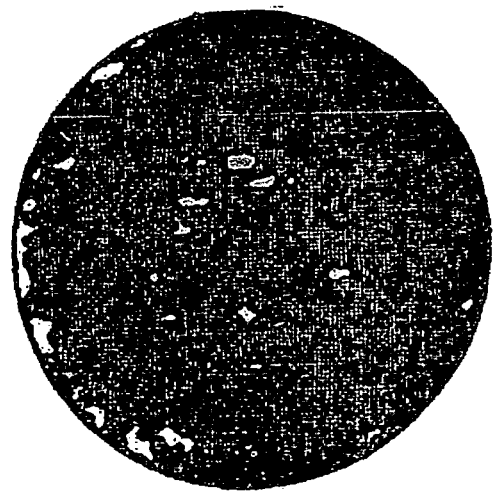

The level of the unevenness of a partition wall surface of the honeycomb structure was inspected by using the device 1 for inspecting unevenness of a partition wall surface of the honeycomb structure as shown in FIG. 1. In the present example, inspection was conducted on three honeycomb structures A, B, and C having different levels of unevenness of a partition wall surfaces of the targeted honeycomb structures 2. The honeycomb structures A, B, and C are in the cylindrical shape having a diameter of an end face of 105.7 mm and a length of 114.3 mm in the central axis direction. FIGS. 7(a) to 7(c) are explanatory view showing an image picked up by the imaging means when the honeycomb structures A, B, and C were inspected by using the device 1 (see FIG. 1) for inspecting unevenness of a partition wall surface of a honeycomb structure. FIGS. 7(a), 7(b), and 7(c) are images of the honeycomb structures A, B, and C, respectively. The gray level of each of the images obtained was subjected to a binary treatment, and thereby the ratio of the area of the portion where the transmitted image was projected deeply to the whole area of the transmitted image in the image was calculated. FIG. 8(a) is an explanatory view showing the result of a binary treatment on the image shown in FIG. 7(a), FIG. 8(b) is an explanatory view showing the result of a binary treatment on the image shown in FIG. 7(b), FIG. 8(c) is an explanatory view showing the result of a binary treatment on the image shown in FIG. 7(c). FIGS. 8(a) to 8(c) shows the portions where the transmitted image was projected deeply, that is, the portions having unevenness on a partition wall surface is shown by white. As the results of the inspection, the ratio of the area of the portion where the transmitted image was projected deeply to the area of the whole transmitted image were 0.1% in the honeycomb structure A, 2.7% in the honeycomb structure B, and 4.2% of the honeycomb structure C. Thus, by using the device 1 (see FIG. 1) for inspecting unevenness of a partition wall surface of the honeycomb structure of the present embodiment, the difference between the honeycomb structures A, B, and C could clearly be inspected.

INDUSTRIAL APPLICABILITY

Inspection on unevenness of a partition wall surface of a honeycomb structure, which serves as a yardstick of judging the quality of the honeycomb structure used as a filter, catalyst carrier, or the like, can be performed simply and nondestructively.

The invention claimed is:
1. A method of inspecting, for each cell, unevenness of a partition wall surface of a cylindrical honeycomb structure having a plurality of cells functioning as passages for fluid and separated from each other by partition walls, the method comprising the steps of:

allowing a diffusion light to enter from one end face side of a honeycomb structure by a predetermined lighting means and to exit from the other end face side of the honeycomb structure after passing it through the inside of the cells;

allowing the exited diffusion light to pass through a translucent screen disposed on the other end face side of the honeycomb structure to act as a transmitted light;

projecting a transmitted image by means of the tone of the transmitted light onto the transmitted light side of the screen;

picking up the transmitted image projected on the screen by an imaging means;

analyzing by an analyzing means the gray level of the obtained image to inspect for each cell the level of the surface unevenness of the partition walls of the honeycomb structure; and obtaining unevenness data of the partition walls from the obtained image.

2. A method of inspecting unevenness of a partition wall surface of a cylindrical honeycomb structure according to claim 1, wherein the screen is disposed so as to be in contact with the other end face side of the honeycomb structure.

3. A method of inspecting unevenness of a partition wall surface of a cylindrical honeycomb structure according to claim 1, wherein the gray level of the image is analyzed by being subjected to a binary treatment with the analyzing means.

4. A method of inspecting unevenness of a partition wall surface of a cylindrical honeycomb structure according to claim 1, wherein a shadow generated by the partition walls in the image is removed before the gray level of the image is analyzed by the analyzing means.

5. A method of inspecting unevenness of a partition wall surface of a cylindrical honeycomb structure according to claim 1, wherein the diffusion light from the lighting means has an illuminance of 3000 Lux or more.

6. A method of inspecting unevenness of a partition wall surface of a cylindrical honeycomb structure according to claim 1, wherein the screen has a light transmittance of 35 to 90%.

7. A method of inspecting, for each cell, unevenness of a partition wall surface of a cylindrical honeycomb structure having a plurality of cells functioning as passages for fluid and separated from each other by partition walls, the method comprising the steps of:

allowing a diffusion light to enter from one end face side of a honeycomb structure by a predetermined lighting means and to exit from the other end face side of the honeycomb structure after passing it through the inside of the cells;

allowing the exited diffusion light to be picked up by an imaging means for each image from the direction perpendicular to the other end face of the honeycomb structure;

analyzing by an analyzing means the gray level of the obtained image to inspect for each cell the level of the surface unevenness of the partition walls of the honeycomb structure; and obtaining unevenness data of the partition walls from the obtained image.

8. A method of inspecting unevenness of a partition wall surface of a cylindrical honeycomb structure according to claim 7, wherein the gray level of the image is analyzed by being subjected to a binary treatment with the analyzing means.

9. A method of inspecting unevenness of a partition wall surface of a cylindrical honeycomb structure according to claim 7, wherein a shadow generated by the partition walls in the image is removed before the gray level of the image is analyzed by the analyzing means.

10. A method of inspecting unevenness of a partition wall surface of a cylindrical honeycomb structure according to claim 7, wherein the diffusion light from the lighting means has an illuminance of 3000 Lux or more.

11. An inspecting device for inspecting, for each cell, unevenness of a partition wall surface of a cylindrical honeycomb structure having a plurality of cells functioning as passages for fluid and separated from each other by partition walls, the inspecting device comprising:

a lighting means disposed on one end face side of the honeycomb structure and allowing a diffusion light to enter from one end face side of a honeycomb structure and to exit from the other end face side of the honeycomb structure after passing it through the inside of the cells;

a translucent screen disposed on the other end face side of the honeycomb structure, allowing the exited diffusion light to pass therethrough to obtain a transmitted light, and capable of projecting a transmitted image by means of the tone of the transmitted light onto the transmitted light side of the screen;

an imaging means for picking up the transmitted image projected on the screen; and an analyzing means for analyzing the gray level of the image picked up by the imaging means to inspect for each cell the level of the surface unevenness of the partition walls of the honeycomb structure.

12. An inspecting device for inspecting unevenness of a partition wall surface of a cylindrical honeycomb structure according to claim 11, wherein the screen is disposed so as to be in contact with the other end face side of the honeycomb structure.

13. An inspecting device for inspecting unevenness of a partition wall surface of a cylindrical honeycomb structure according to claim 11, wherein the gray level of the image is analyzed by being subjected to a binary treatment with the analyzing means.

14. An inspecting device for inspecting unevenness of a partition wall surface of a cylindrical honeycomb structure according to claim 11, wherein a shadow generated by the partition walls in the image is removed before the gray level of the image is analyzed by the analyzing means.

15. An inspecting device for inspecting unevenness of a partition wall surface of a cylindrical honeycomb structure according to claim 11, wherein the diffusion light from the lighting means has an illuminance of 3000 Lux or more.

16. An inspecting device for inspecting unevenness of a partition wall surface of a cylindrical honeycomb structure according to claim 11, wherein the screen has a light transmittance of 35 to 90%.

17. An inspecting device for inspecting, for each cell, unevenness of a partition wall surface of a cylindrical honeycomb structure having a plurality of cells functioning as passages for fluid and separated from each other by partition walls, the inspecting device comprising:

a lighting means disposed on one end face side of the honeycomb structure and allowing a diffusion light to enter from one end face side of a honeycomb structure and to exit from the other end face side of the honeycomb structure after passing it through the inside of the cells;

an imaging means disposed on the other end face side of the honeycomb structure and allowing the exited diffusion light to be picked up for each cell from the direction perpendicular to the other end face of the honeycomb structure; and an analyzing means for analyzing the gray level of the image picked up by the imaging means to inspect for each cell the level of the surface unevenness of the partition walls of the honeycomb structure from a result of analysis by the analyzing means.

18. An inspecting device for inspecting unevenness of a partition wall surface of a cylindrical honeycomb structure according to claim 17, wherein the gray level of the image is analyzed by being subjected to a binary treatment with the analyzing means.

19. An inspecting device for inspecting unevenness of a partition wall surface of a cylindrical honeycomb structure according to claim 17, wherein a shadow generated by the partition walls in the image is removed before the gray level of the image is analyzed by the analyzing means.

20. An inspecting device for inspecting unevenness of a partition wall surface of a cylindrical honeycomb structure according to claim 17, wherein the diffusion light from the lighting means has an illuminance of 3000 Lux or more.

* * * * *